(12) United States Patent  (10) Patent No.: US 8,237,124 B2
Marwala et al.  (45) Date of Patent: Aug. 7, 2012

(54) CODED APERTURE MASKS FOR RADIATION-BASED MEDICAL IMAGING

(75) Inventors: Tshilidzi Marwala, Douglasdale (ZA); David Milton Rubin, Lower Houghton (ZA); David Mark Starfield, Victory Park (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 160 days.

(21) Appl. No.: 12/601,285

(22) PCT Filed: May 22, 2008

(86) PCT No.: PCT/IB2008/001278
§ 371 (c)(1), (2), (4) Date: Feb. 23, 2010

(87) PCT Pub. No.: WO2008/142543
PCT Pub. Date: Nov. 27, 2008

(65) Prior Publication Data
US 2011/0190616 A1  Aug. 4, 2011

(30) Foreign Application Priority Data
May 23, 2007 (ZA) ................. 2006/09746
May 24, 2007 (ZA) ................. 2007/02171

(51) Int. Cl.
*G01T 1/164* (2006.01)
(52) U.S. Cl. ................. 250/363.06
(58) Field of Classification Search ............. 250/363.06, 250/363.1
See application file for complete search history.

(56) References Cited

U.S. PATENT DOCUMENTS

2002/0075990 A1  6/2002  Lanza et al.
2006/0108509 A1  5/2006  Frangioni et al.
2006/0261278 A1  11/2006  Accorsi

FOREIGN PATENT DOCUMENTS
WO   2007/054769 A2   5/2007

OTHER PUBLICATIONS

Starfield, et al., "High-Transparency Coded Apertures in Planar Nuclear Medicine Imaging: Experimental Results", Nuclear Science Symposium Conference Record, 2007, NSS, 07, IEEE, IEEE, PI, Oct. 1, 2007, pp. 3151-3157.
International Search Report for PCT/IB2008/001278, dated Nov. 5, 2008.
Accorsi et al., "Toward a Medipix2 Coded Aperture Gamma Microscope," Nuclear Science Symposium Conference Record, 2004 IEEE, Oct. 16-22, 2004, pp. 2461-2464, vol. 4.

*Primary Examiner* — David Porta
*Assistant Examiner* — Marcus Taningco
(74) *Attorney, Agent, or Firm* — Nixon Peabody LLP

(57) ABSTRACT

This invention relates to a coded aperture mask for use in diagnostic nuclear medicine imaging. The coded aperture mask consists of a sheet of radiation opaque mask material having a series of apertures extending therethrough. The thickness of mask material has an attenuation percentage of less than 75% and, in a preferred embodiment, about equal to 29%. The coded aperture mask also, in a preferred embodiment, has a lead attenuation tube and has a projection of the smallest hole occupying the same area as a single pixel of a detector. The invention extends to a diagnostic nuclear medicine imaging system which uses a 16 bit gamma camera as a radiation detector.

26 Claims, 11 Drawing Sheets

An illustration of a projected array of impulses, all equal in amplitude, measured by specific pixels of the detector;

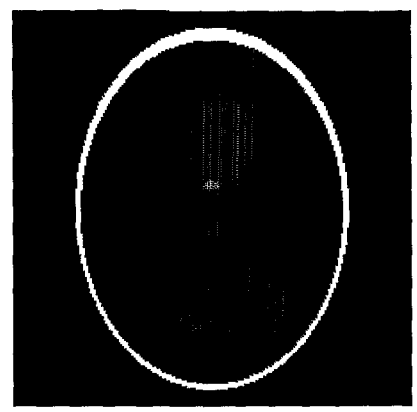
Figure 1. A high contrast digital Shepp-Logan phantom.
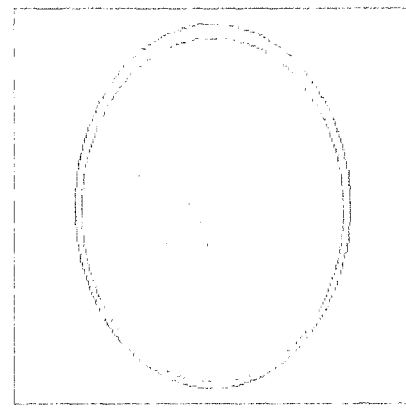
Figure 2. A low contrast digital Shepp-Logan phantom.
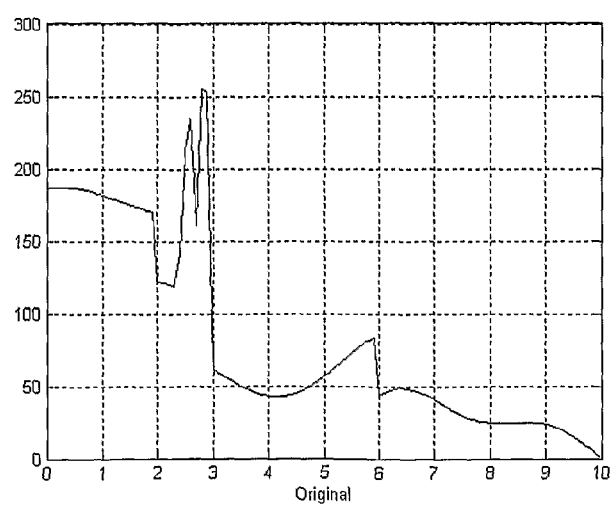
Figure 3. An example of a 2D analogue signal.

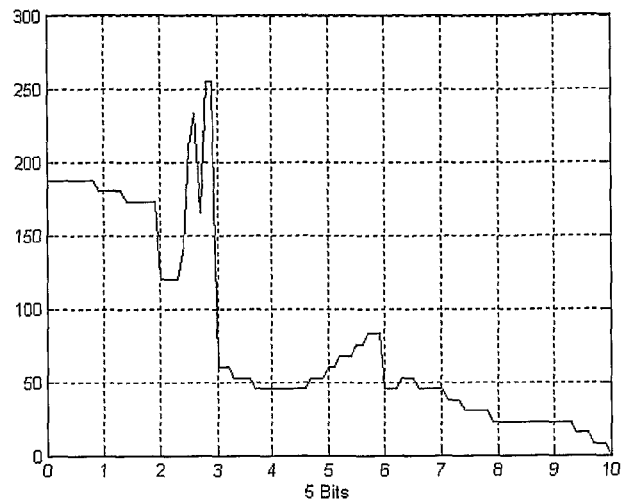
Figure 4. Digitisation of the signal of Figure 3 with a 5-bit resolution on the vertical axis.
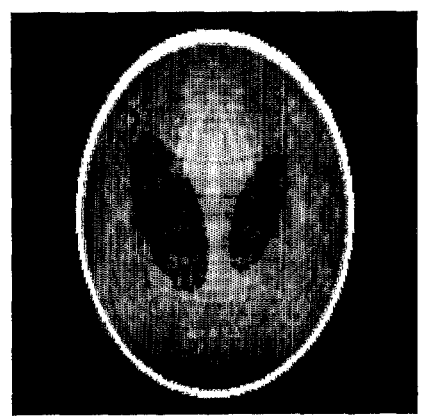
Figure 5. 97 % attenuation image, for an 8-bit (256 value) gamma camera

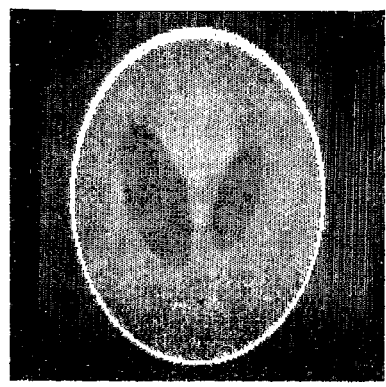
Figure 6. 29 % attenuation image, for an 8-bit (256 value) gamma camera
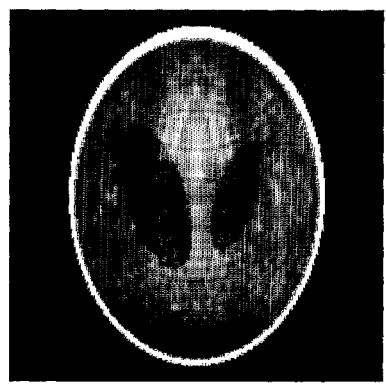
Figure 7. 97 % attenuation image, for a 16-bit (65536 value) gamma camera
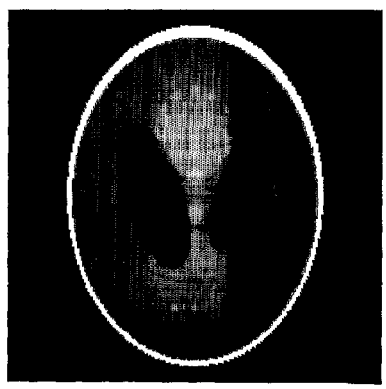
Figure 8. 29 % attenuation image, for a 16-bit (65536 value) gamma camera

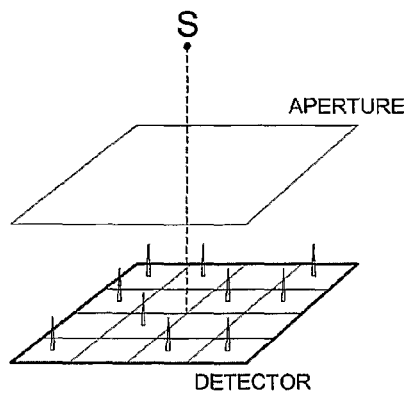
Figure 9. An illustration of a projected array of impulses, all equal in amplitude, measured by specific pixels of the detector;
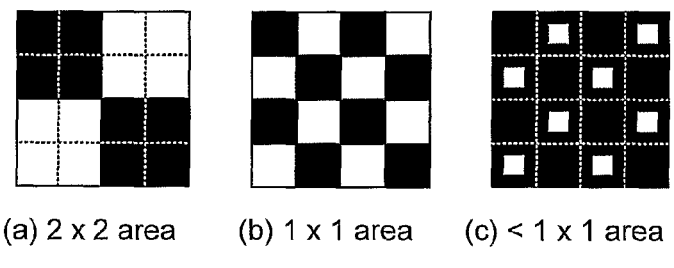
(a) 2 x 2 area    (b) 1 x 1 area    (c) < 1 x 1 area
Figure 10. An illustration of idealised perfectly aligned aperture patterns projected onto a detector, for varying illumination areas, where the dotted lines represent detector pixel boundaries

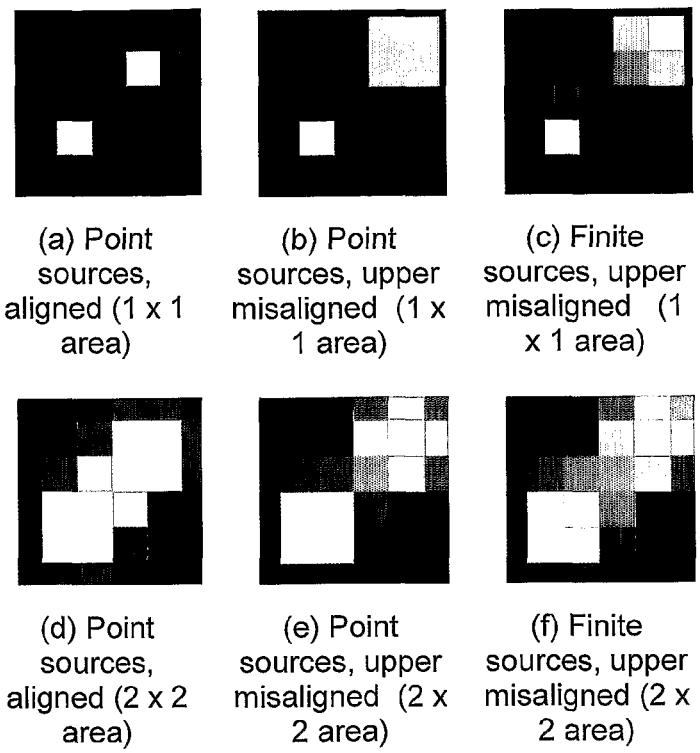
Figure 11. Simulation results for discrete point sources positioned on the image diagonal, both aligned and misaligned, together with finite sources
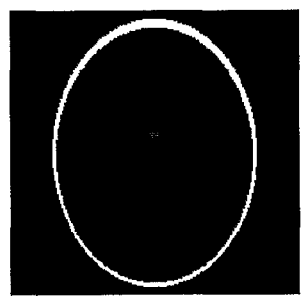
Figure 12. 2D digital Shepp-Logan phantom
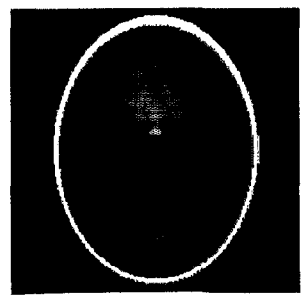
Figure 13. Perfect PSF (infinitely small area), RMSE of 16 %

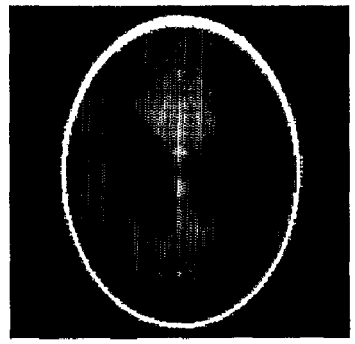
Figure 14.   Perfect PSF (1 x 1 area), RMSE of 23 %
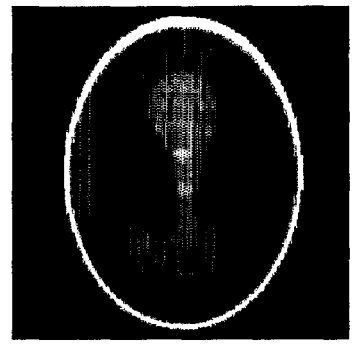
Figure 15.   Perfect PSF (2 x 2 area), RMSE of 28 %
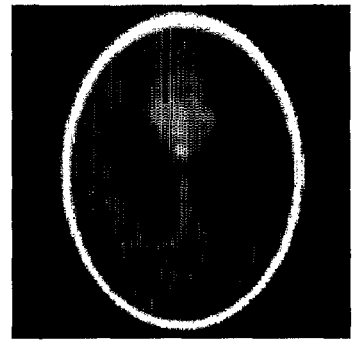
Figure 16.   $\sigma$ = 1.27 PSF (1 x 1 area), RMSE of 25 %
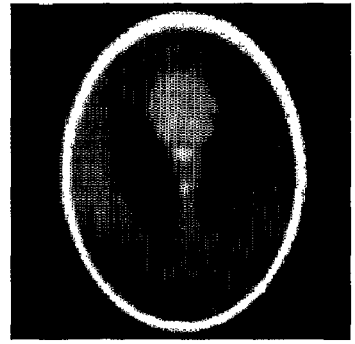
Figure 17.   $\sigma$ = 1.27 PSF (2 x 2 area), RMSE of 34 %

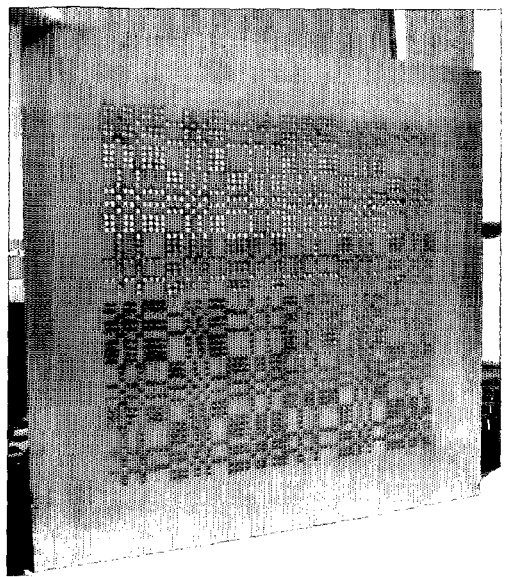

Figure 18. A photograph of an opaque aperture constructed from tungsten of thickness 1 mm, corresponding to an attenuation of 97 % used in an experimental study to verify the theoretical postulations made

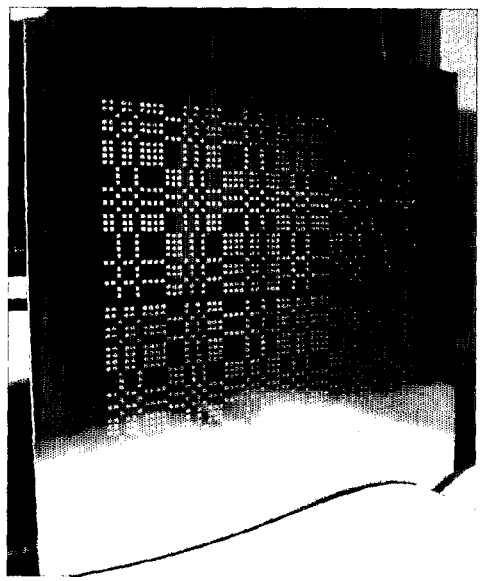

Figure 19. A photograph of a highly transparent aperture constructed from tungsten of thickness 100 μm, corresponding to an attenuation of 29 % used in an experimental study to verify the theoretical postulations made

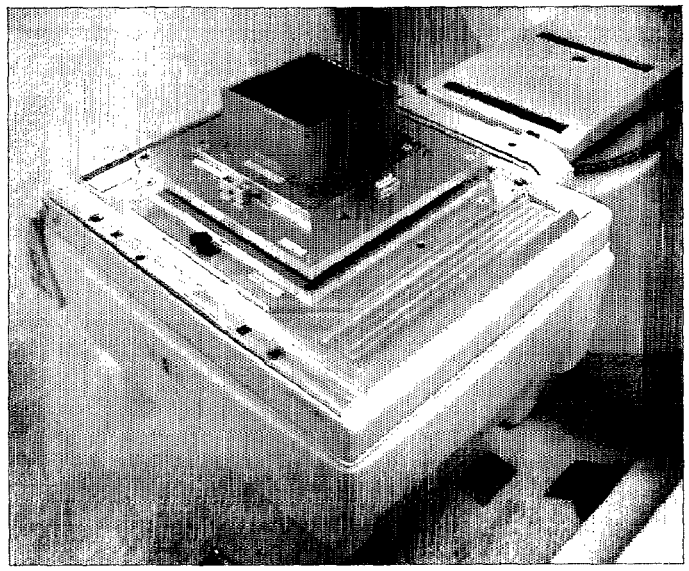
Figure 20. A photograph of a specialized aluminium gamma camera frame that was designed for the described experimental study
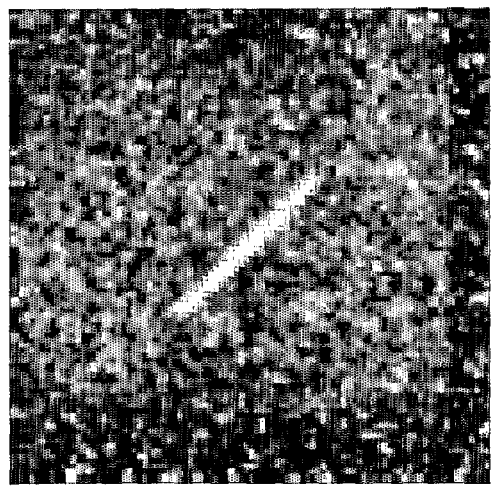
a

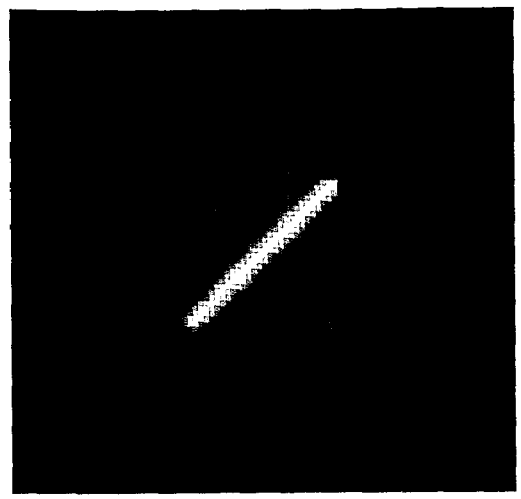
b
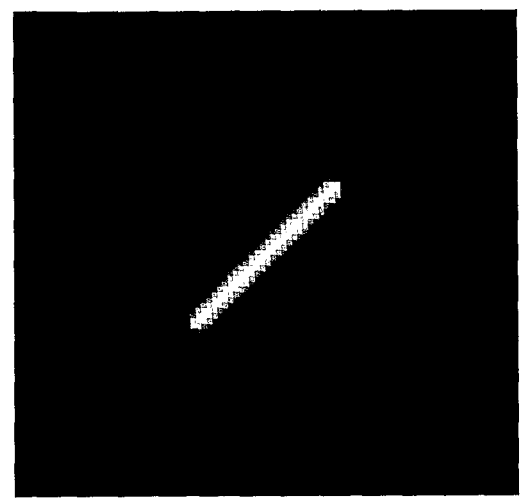
c
Figures 21a, b and c.    a series of simulated images, through a 29% attenuation mask of a digital phantom developed in order to allow for comparison with the experimental data where all simulation factors with the exception of the acquisition bit depth were held constant

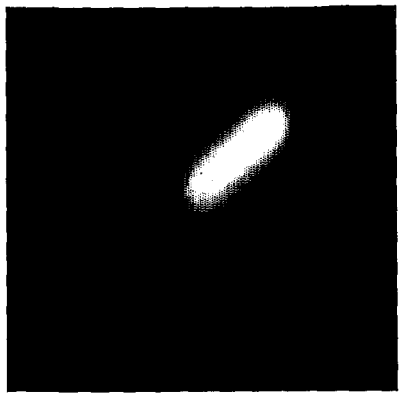
Figure 22. A low energy high resolution (LEHR) collimator image used as a point of reference in the experiment
Figure 23. Opaque (97% attenuation) coded aperture image at a maximum pixel count of 286, 45 seconds, showing some noise
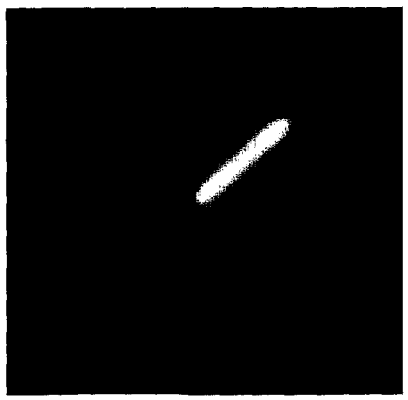
Figure 24. Opaque (97% attenuation) coded aperture image at a maximum pixel count of 3270, 10 minutes

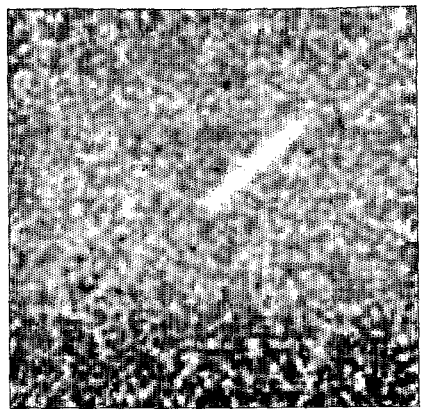
Figure 25. Transparent (29% attenuation) coded aperture image at a maximum pixel count of 285, 30 seconds
Figure 26. Transparent (29% attenuation) coded aperture image at a maximum pixel count of 8248, 15 minutes

CODED APERTURE MASKS FOR RADIATION-BASED MEDICAL IMAGING

FIELD OF THE INVENTION

This invention relates to coded aperture masks for use in radiation-based medical imaging and, more particularly, in diagnostic nuclear medical imaging.

BACKGROUND TO THE INVENTION

Coded aperture masks consist of a pattern of apertures or pin holes in a material that has a high attenuation coefficient for a type of radiation used in diagnostic nuclear medicine imaging. Where, for example, gamma-rays, the array of apertures is arranged in a material such as tungsten which, typically, is 1-2 mm in thickness. The mask is formed by about 88 000 apertures arranged in a pre-determined manner on and extending through the tungsten sheet.

Coded aperture masks may be and are used as an alternative to various types of collimators, particularly lead collimators, in gamma-ray imaging. Lead collimators are, essentially, grid-like screens made of lead. The apertures of the grid are configured to permit transmission of parallel or near parallel gamma-rays produced by a gamma radiation source to a detector or imaging means which is typically a gamma camera. Lead and other collimators generally suffer from low resolution and attempts to increase resolution result in lowered efficiency. It is for this reason that attempts are being made to use coded aperture masks to replace lead collimators.

In addition, coded aperture masks have the potential to increase the signal-to-noise ratio (SNR) of the imaging system [1], and can, thus, theoretically be applied advantageously to diagnostic imaging in nuclear medicine. The increased SNR can be manipulated to improve image resolution, to shorten imaging time, or to reduce the patient's dose of radioactivity. The advantages of this are self evident.

Coded aperture masks have been used extensively in astrophysics, where far-field imaging conditions apply. Such conditions allow for the acquisition of images that are close to perfect for two-dimensional (2D) noise-free data [2]. Unfortunately the same cannot be said for the near-field conditions of nuclear medicine where corruption of the image by near-field artifacts is a universal problem.

Previous research has provided an indication of characteristics of apertures that are optimal for the purposes of nuclear medicine [3]. A reduction of near-field artifacts can be achieved by taking a second image with a rotated aperture, and by then summing the two sets of data obtained [4]. The use of an array of limited field-of-view coded apertures has also been shown to have the potential to significantly reduce near-field artifacts [5].

Coded aperture imaging requires that for each point of the source, the aperture pattern must be projected onto a detector. This results in overlapping aperture patterns, each shifted and weighted according to the location and the intensity of the specific point source that projected the pattern [6]. Theoretically, this acquisition process is modeled by convolving the source with the aperture pattern. The image is reconstructed by correlating the encoded data with the original coded aperture pattern [6]. This pattern is designed such that a unique reconstruction exists.

Convolution implies that a point source must be imaged equally by each pinhole of the coded aperture, without a change in intensity, and with the image of the point source falling directly below the pinhole. The decoding procedure performs correctly under these conditions, but in practice the convolution model does not hold. The near-field conditions of nuclear medicine introduce artifacts to the image. Further, the thickness of the coded aperture contributes to near-field artifacts, by collimating gamma-rays that have high angles of incidence.

With respect to image resolution, the pixel size is typically related to the size of the projection of the smallest hole in the coded aperture. The size of the smallest hole is typically designed in relation to the resolution of the gamma camera. This means that a gamma camera with 10× the resolution of existing gamma cameras, for example, can theoretically have a coded aperture that matches the 10× improvement. However, due to collimation artifacts, the minimum size of the hole is limited by the thickness of the aperture material. Similarly, the thickness of the coded aperture also constrains the manufacturing technique that can be used. Typically in laser drilling, the dimensions of the holes have to be greater than the thickness of the material, whilst a thickness of 1 mm, for example, is generally unsuitable either for etching or for deposition.

More importantly, the resolution of the resultant image is constrained, inter-alia, by the dimensions of the holes, which are in turn constrained by the thickness of the aperture material which is related to the attenuation properties of that material. If a gamma-ray passes through opaque aperture material of density $\rho$, with an attenuation coefficient $\mu$ specific for a given element at the energy of interest, and an effective thickness $r_m$, the transmission t of the aperture material is given by:

$$t = e^{-\rho \mu r_m} \quad (1)$$

The ability of the aperture material to block gamma-rays is then given by the attenuation $\alpha$:

$$\alpha = 1 - t \quad (2)$$

For a given source of radioactivity, with an associated energy, the thickness of the coded aperture material is typically chosen to give an attenuation of more than 90%, frequently 99%.

In addition to the above and with respect to image resolution, it is necessary to consider a point source that is projected through an infinitely small pinhole onto a perfect detector. If the projection is recorded by a single pixel of the detector, the representation will be correct. If the projection falls on a boundary between neighbouring pixels, counts of radioactivity will be distributed equally between those pixels. The total number of counts remains unchanged, but the measured peak is no longer representative of reality.

This problem is known as the 'partial volume effect' [10], and is related to the digitisation of an analogue signal. A solution is to increase the radius of the pinhole, such that the projection of the point source illuminates an area that corresponds to at least 2×2 pixels of the detector [6]. In this manner, one pixel is always fully illuminated, and the measured peak will be correct.

With respect to image resolution, the pixel size is typically related to the size of the projection of the smallest hole in the coded aperture. The size of the projection of the smallest hole is typically designed in relation to the resolution of the gamma camera, with the projection typically occupying the same area as at least a 2×2 array of detector pixels [6], in order to counter the partial volume effect.

Please note that while it is understood in the art to which this invention relates that nuclear medicine imaging refers to imaging using radioactive tracers, typically introduced into the body of the subject being imaged, the applicant wishes to emphasize that the invention also applies to radiation-based medical imaging, where the rays may include other forms of radiation in medical imaging, for example, X-rays produced in an X-ray tube outside the body being imaged, or a radioactive source outside the body producing gamma rays for imaging the body. Images can be produced from ingested radioactive tracers or from a source outside the body being imaged.

OBJECT OF THE INVENTION

It is an object of this invention to provide a coded aperture mask for use in diagnostic nuclear medicine imaging which, at least partly, reduces collimation artifacts encountered with prior art masks and, consequently, can simultaneously improve image resolution.

SUMMARY OF THE INVENTION

In accordance with this invention there is provided a coded aperture mask for use in radiation-based medical imaging comprising a sheet of radiation opaque mask material having a series of apertures extending therethrough, the thickness of mask material having an attenuation percentage of less than 75%.

There is also provided for the mask material to have an attenuation percentage of less than 50% and, preferably, less than 30%.

There is further provided for the coded aperture mask to be used for imaging gamma-rays, for the sheet of radiation mask material, by way of example, to be a sheet of metal selected from the group consisting of tungsten, gold, lead and platinum and, where the metal is tungsten, for it to have a thickness of 100 μm (which is largely transparent) for imaging Technetium-99m (which has an energy of 140 keV), where the metal is gold, for it to have a thickness of 90 μm (which is largely transparent) for imaging Technetium-99m (which has an energy of 140 keV), where the metal is lead, for it to have a thickness of 130 μm (which is largely transparent) for imaging Technetium-99m (which has an energy of 140 keV), and, where the metal is platinum, for it to have a thickness of 80 μm (which is largely transparent) for imaging Technetium-99m (which has an energy of 140 keV).

There is further provided for the coded aperture to have a projection of the smallest hole occupying the same area as a single pixel of the detector.

There is also provided for a radiation attenuating tube to extend about each coded aperture mask in the direction of the axes of the apertures therein.

Further features of the invention provide for each tube to extend from either side of the respective masks; for each tube to have parallel sides; and for the masks to be carried on one sheet of material.

Still further features of the invention provide for multiple coded apertures to be arranged in an array which is from a 3 by 3 to a 5 by 5 array; for the coded aperture masks to be configured for gamma rays, preferably gamma rays having an energy of 140 keV; for the coded aperture masks to be made of tungsten, and tubes to be made of lead; for the tungsten to have a thickness of 100 μm; for the lead to have a thickness of 1 to 2 mm; and for each tube to extend up to 50 cm, preferably 10 cm, on either side of the array.

The invention extends to a radiation-based medical imaging system comprising a radiation source, a coded aperture mask as described above, and a radiation detector.

There is further provided for the radiation source to be a gamma-ray radiation source and for the radiation detector to be a gamma camera, preferably a 16 bit gamma camera.

BRIEF DESCRIPTION OF THE DRAWINGS

Embodiments of the invention will be described below with reference to the accompanying drawings in which:

FIG. 1 is a high contrast digital Shepp-Logan phantom;

FIG. 2 is a low contrast digital Shepp-Logan phantom;

FIG. 3 is an example of a 2D analogue signal;

FIG. 4 is an illustration of the signal of FIG. 3 digitised with 5-bit resolution on the vertical axis;

FIG. 5. is a simulation of a 97% attenuation aperture image of a digital Shepp-Logan phantom, for an 8-bit (256 value) gamma camera;

FIG. 6. is a simulation of a 29% attenuation aperture image of a digital Shepp-Logan phantom, for an 8-bit (256 value) gamma camera;

FIG. 7. is a simulation of a 97% attenuation aperture image of a digital Shepp-Logan phantom, for a 16-bit (65536 value) gamma camera;

FIG. 8. is a simulation of a 29% attenuation aperture image of a digital Shepp-Logan phantom, for a 16-bit (65536 value) gamma camera;

FIG. 9. is an illustration of a projected array of impulses, all equal in amplitude, measured by specific pixels of the detector;

FIG. 10. is an illustration of idealised perfectly aligned aperture patterns projected onto a detector, for varying illumination areas, where the dotted lines represent detector pixel boundaries;

FIG. 11. shows simulation results for discrete point sources positioned on the image diagonal, both aligned and misaligned, together with finite sources;

FIG. 12. is a representation of an ideal digitized 2D Shepp-Logan phantom;

FIG. 13. is a simulation of the Shepp-Logan phantom of FIG. 12 for a perfect detector PSF (infinitely small projection area), RMSE of 16%;

FIG. 14. is a simulation of the Shepp-Logan phantom of FIG. 12 for a perfect detector PSF (1×1 projection area), RMSE of 23%;

FIG. 15. is a simulation of the Shepp-Logan phantom of FIG. 12 for a perfect detector PSF (2×2 projection area), RMSE of 28%;

FIG. 16. is a simulation of the Shepp-Logan phantom of FIG. 12 for a σ=1.27 detector PSF (1×1 projection area), RMSE of 25%;

FIG. 17. is a simulation of the Shepp-Logan phantom of FIG. 12 for a σ=1.27 detector PSF (2×2 projection area), RMSE of 34%;

FIG. 18. is a photograph of an opaque aperture constructed from tungsten of thickness 1 mm, corresponding to an attenuation of 97% used in an experimental study to verify the theoretical postulations made;

FIG. 19. is a photograph of a highly transparent aperture constructed from tungsten of thickness 100 μm, corresponding to an attenuation of 29% used in an experimental study to verify the theoretical postulations made;

FIG. 20. A photograph of a specialized aluminium gamma camera frame that was designed for the described experimental study;

FIGS. 21a, b and c. are a series of simulated images through a 29% attenuation mask of a digital phantom developed in order to allow for comparison with the experimental data where all simulation factors with the exception of the acquisition bit depth were held constant;

FIG. 22. is a low energy high resolution (LEHR) collimator image used as a point of reference in the experiment;

FIG. 23. is an opaque (97% attenuation) coded aperture image at a maximum pixel count of 286, 45 seconds, showing some noise;

FIG. 24. is an opaque (97% attenuation) coded aperture image at a maximum pixel count of 3270, 10 minutes;

FIG. 25. is a transparent (29% attenuation) coded aperture image at a maximum pixel count of 285, 30 seconds; and FIG. 26. is a transparent (29% attenuation) coded aperture image at a maximum pixel count of 8248, 15 minutes.

DETAILED DESCRIPTION OF THE INVENTION

Current thinking with respect to nuclear medicine imaging and percentage attenuation derives from the use of collimators which collimate rays but which cease to function correctly at lower percentages of attenuation of the rays and this has, to a large extent, militated against the use of coded aperture masks which have lower percentages of attenuation of the rays. This line of thinking has been carried over to imaging using coded apertures and there are two likely reasons for this:

1. In coded aperture imaging, each point of the source projects the coded aperture pattern onto a detector. The shadow of the coded aperture is projected with the greatest contrast when the attenuation is at 100%. Decreasing the attenuation percentage increases the penetration of the coded aperture by the gamma-rays, and results in a lighter shadow, with less contrast. The encoded image becomes less visible. This is seen if one compares the Shepp-Logan phantoms illustrated in FIGS. 1 and 2; and
2. A gamma detector is not continuous (analogue) in measurement, but rather has a specific number of values that can be measured (it is discreet). Decreasing the contrast in the detected image results in a decrease in the number of values that can be measured, and an associated loss of accuracy. This is illustrated in the 2D plots in FIGS. 3 and 4.

Central to the current invention is the theory that the current line of thinking as outlined above is not entirely correct. The reasons for this are as follows:

1. The contrast of the projected image, which is encoded, is of little significance. This is because the decoded image, which is obtained by correlation, results from searching for the expected pattern. Provided that the pattern is recognisable, there will be no loss of contrast in the decoded image.
2. Quantisation of the measured values decreases the quality of the encoded image. This decreases the likelihood of the pattern being recognisable, which results in noise in the decoded image. This is strictly dependent on the number of values (related to the number of bits) that can be measured. Provided that there are a sufficient number of values available (or enough discrete levels), there should be no loss of quality in the decoded image.

To test this thinking, a computer simulator based on ray tracing techniques, and capable of predicting image acquisition in the field of nuclear medicine, was developed. Computer simulation results for a digital Shepp-Logan phantom [7] are presented.

A high contrast digital Shepp-Logan phantom is clearly visible (FIG. 1). Lowering the contrast reduces the visibility of the image (FIG. 2), as well as the viewer's ability to discern features within the image.

With respect to quantisation, a 2D signal is shown by way of example (FIG. 3). If the vertical axis has only a 5-bit resolution available, the signal can no longer be represented with the same degree of accuracy (FIG. 4).

In the results that follow, the only variation is the transparency of the coded aperture, and the number of bits of the gamma camera. That is aperture material, aperture type, dimensions of the holes, near-field geometry, and decoding procedure remain unaltered. The results are by way of example only, and are based on the energy of Technetium-99m (140 keV), and a tungsten coded aperture.

8-bit 97% attenuation: The figure of 97% corresponds to a material thickness of 1 mm. There is no loss of either contrast or image quality in the encoded image. The resultant decoded image (FIG. 5) is affected by near-field artifacts, and image quality is related to the coded aperture type. An 8-bit gamma camera has a maximum of 256 measurable values.

8-bit 29% attenuation: The figure of 29% corresponds to a material thickness of 100 μm. The low contrast encoded image results in a loss of accuracy. The projected coded aperture pattern is not sufficiently recognisable, and the decoded image is affected by noise (FIG. 6).

16-bit 97% attenuation: Compared to an 8-bit gamma camera, a 16-bit camera has 256× the number of measurable values. The attenuation of the coded aperture material is sufficient to prevent a loss of contrast, and the additional measurable values have little impact on the quality of the decoded image (FIG. 7).

16-bit 29% attenuation: The encoded image suffers from both a loss of contrast and a loss of accuracy. Being a 16-bit gamma camera, however, there are a sufficient number of measurable values for the projected coded aperture pattern to remain recognisable. As a result, the decoded image is not affected by noise (FIG. 8). There is also a simultaneous reduction of collimation artifacts. This image is acquired by incorporating the principals described in this invention.

It is suggested that the above simulation results show that a highly transparent coded aperture adds noise to the image, when the gamma camera has an insufficient number of measurable values. A gamma camera with 2× the number of bits appears to result in little improvement to image quality, when imaging with the prior art coded aperture.

Acquiring the image under the same conditions, but with the use of a highly transparent coded aperture (such as is described in this invention), together with a 16-bit gamma camera, does not add noise to the image, and simultaneously reduces collimation artifacts.

These results show that a highly transparent coded aperture can be used, without loss of image quality, when the gamma camera has a sufficient number of measurable values. At this time, gamma cameras typically feature 16-bits (as opposed to the 8-bits of an earlier generation of gamma cameras).

An aperture that is 10× thinner makes possible several (previously problematic) avenues of manufacture. Of more significance is image resolution, as an aperture that is 10× thinner automatically allows for a 10× improvement in image resolution. In this case the gamma camera would become the limiting factor, but there are already some indications that gamma cameras may be able to follow suit [8].

The only change between the 16-bit gamma camera test scenarios was that a high attenuation coded aperture was replaced with a highly transparent coded aperture. From a practical perspective, such a change can readily be made. It is anticipated that this will enhance the practicality of coded aperture imaging in the field of nuclear medicine.

It should be noted that coded apertures with thicknesses in the μm range have been developed for imaging at lower radiation energies [8, 9]. At these energies, the thickness of the coded apertures is such as to still yield a high percentage of attenuation, in accordance with the prior art.

In addition to the above and when each of the multiple transparent elements of a coded aperture acts and is considered as an independent hole, with each casting a projection of the source onto the detector. As such, the partial volume effect is applicable to the recorded coded aperture image [6].

In order to decode the overlapping projections, it is necessary to consider the situation from another perspective, which is as each point of the source projecting the coded aperture pattern onto the detector [6]. Provided that the pattern has specific properties, it is possible to uniquely decode the encoded data.

The coded aperture pattern is a discrete binary array [1]. The decoding procedure therefore operates not in the continuous domain, but rather on the sampled measured data. This means that for a point source, a perfect reconstruction would be achieved if the projected coded aperture pattern were sampled as a single array of impulses or delta functions, all equal in amplitude, as indicated in FIG. 9.

The closest approximation to projecting a set of impulses would be with the use of an idealised infinitely thin but completely opaque coded aperture, having infinitely small pinholes.

Consider three parallel planes representing the source, the coded aperture, and the detector. If the grids representing the discrete points of the source, the pinholes of the coded aperture, and the pixels of the detector are all perfectly aligned, a perfect detector will measure the desired sets of impulses in the pattern of the coded aperture.

If these three grids are not perfectly aligned, the shift causes the impulses to fall away from the centre of each pixel. The resultant interpolation is equivalent to the measurement of overlapping impulse patterns. The impulses of an individual pattern will ideally have the same amplitudes, but this amplitude is reduced as a result of the partial volume effect.

If the infinitely small pinholes are replaced with transparent coded aperture elements, such that each element illuminates a 1×1 pixel area of the detector, blur is then increased, but the system becomes less susceptible to the partial volume effect.

Regardless of the alignment of the three grids, the partial volume effect is completely removed by applying the prior art technique of illuminating a 2×2 pixel area of the detector [6]. However, the increased area of the projection results in the measurement of neighbouring impulse patterns, and thus in further blurring of the reconstructed image.

Gamma camera pixel size clearly sets the first limit on image resolution—this being the closest spacing at which samples can be obtained. The partial volume effect sets the second limit, as its solution requires the illumination of an area corresponding to 2×2 pixels of the detector. The point spread function (PSF) of the detector further contributes to these limitations.

Transparent coded aperture elements are designed with respect to the pixel size of a specific gamma camera. Sub-optimal patterns can be remedied without affecting the open fraction, as this remains constant for a given family of coded apertures. The dimensions of the transparent elements can be decreased for a higher resolution system, and the number of elements in the array can be increased, such that both the field-of-view and the open fraction of the material are maintained.

There is no trade-off between resolution and imaging efficiency, provided that the illuminated area is not below that of a single detector pixel. At this sampling threshold the number of elements in the array can no longer be increased. The concept is illustrated in FIG. 10. Apart from the partial volume effect, a coded aperture designed to illuminate a 1×1 pixel area of the detector gives a resolution that is optimal without compromising efficiency.

Consider the scenario of a source having a finite spatial extent, with the system maintaining ideality in all other respects. A finite source increases the illuminated area, and assists with countering the partial volume effect—as would be the case for the effectively continuous objects that are imaged in nuclear medicine. While a grid representing discrete points of the source may be useful for computational purposes, multiple grids of varying shifts would be necessary in order to represent continuity.

Our theory associated with the invention is that a realistic source, coupled with an optimal coded aperture, not only limits the partial volume effect, but also allows for the enhancement of system resolution.

This thinking was tested by means of a ray-tracing computer simulator. The coded apertures were taken as being infinitely thin and completely opaque, with the aim of omitting the artifacts that are introduced by the use of realistic apertures. A perfect detector PSF was used, unless stated otherwise.

Discrete point sources, both perfectly aligned and misaligned, were investigated for varying illumination areas of the detector, together with the simulation of distributed objects. A detector PSF was also applied to the encoded distributed images, so as to allow for testing of the methodology under the presence of increased blur.

The results are based on near-field imaging conditions. Accorsi's method for the reduction of near-field artifacts [4] was applied to all images.

Two digital point sources were positioned on the image diagonal. The source grid was perfectly aligned with respect to the rest of the system. A 1×1 area projection (FIG. 11(a)) gives a sharper image than a 2×2 area projection (FIG. 11(d)). The peak intensities are measured correctly in both cases.

The worst-case partial volume effect is obtained by shifting only the upper source by half a pixel along both axes. The effect is clearly visible for a 1×1 area projection (FIG. 11(b)). The peak of the shifted source remains unaffected for a 2×2 area projection (FIG. 11(e)), but the peak of the stationary source is lower by comparison. Finite sources were represented by superimposing a second point source grid over the first; shifted one quarter of a pixel along both axes. The partial volume effect is less severe for a 1×1 area projection (FIG. 11(c)), relative to FIG. 11(b). For a 2×2 area projection (FIG. 11(f)) the peak of the stationary source has increased, relative to FIG. 11(e), but the blur remains.

A two-dimensional slice of the digital Shepp-Logan phantom [7] was used for the simulation of distributed objects (FIG. 12). The phantom was represented computationally as a grid of point sources, shifted by half a pixel along both axes for worst-case alignment. The results are quantified by means of a root-mean-square error (RMSE), which is computed over the entire image, and is based on the percentage by which pixels differ from the pixels of the phantom [11].

In the results that follow, the only variations are the dimensions of the coded aperture holes. That is aperture material, aperture type, aperture thickness, near-field geometry, and decoding procedure remain unaltered. The results are by way of example only.

A theoretical aperture with infinitely small pinholes is not practical in terms of efficiency, but gives a reconstruction that is close to perfect (FIG. 13).

With reference to the infinitely small holes, a 1×1 area projection is blurred (FIG. 14), but gives a sharper image and a lower RMSE than a 2×2 area projection (FIG. 15).

A blurring detector PSF having σ=1.27 pixels was then applied to the encoded images, prior to decoding. Although the blur makes any resolution improvement difficult to discern visually, a 1×1 area projection (FIG. 16) gives a lower RMSE than a 2×2 area projection (FIG. 17).

The above described simulation results show that an idealised coded aperture having infinitely small pinholes, used in conjunction with a gamma camera having a perfect PSF, does not give a perfect image. The suggested reasons are twofold. Firstly a worst-case alignment of the system grids was used. Secondly, a near-field imaging geometry means that for a single point source, the projected impulse array will no longer have impulses of equal amplitudes [5]. This is one cause of near-field artifacts.

Coded apertures having finite transparent elements make it possible to adjust image resolution without affecting system efficiency, provided that the elements illuminate an area that is not below that of a single detector pixel. This allows a 2×2 area projection (the prior art coded aperture) to be replaced with a 1×1 area projection (such as is described in this invention)—a methodology that both enhances resolution, and reduces the RMSE measurement.

Significant blur minimises the resolution improvement. Nevertheless, the RMSE indicates that a 1×1 area projection remains preferable.

The simulation results show that resolution can be enhanced by illuminating a 1×1 pixel area of the detector. This has been quantified by a root-mean-square error measurement. Furthermore, the partial volume effect has less influence on sources that are of finite dimensions, and the results show no significant influence on distributed sources such as those imaged in nuclear medicine diagnostics.

The only change between the test scenarios was that a 2×2 pixel area projection coded aperture was replaced with 1×1 pixel area projection coded aperture. From a practical perspective, such a change can readily be made. It is anticipated that this will enhance the practicality of coded aperture imaging in the field of nuclear medicine.

It should be noted that coded apertures with small holes have been developed for imaging at high resolution [8]. At the chosen imaging geometry, the size of the holes is such as to still yield a minimum of a 2×2 pixel area projection, in accordance with the prior art.

The above theoretical investigation was tested experimentally using a coded aperture mask designed with respect to a Philips Axis—dual head variable angle gamma camera, for the energy of $^{99m}$Tc (Technetium-99m which has an energy of 140 keV). A self-supporting pattern was used, from the no-two-holes-touching (NTHT) modified uniformly redundant array (MURA) family of coded apertures [6]. The pattern has an open fraction of 12.5% and is based on a 61×61 mosaic, which is pattern centered and anti-symmetric. This allows for near-field artifact reduction by rotation of the aperture [4].

Technical and practical challenges are associated with coded aperture construction. Materials with high attenuation characteristics include uranium, platinum, gold, tungsten and lead. The aperture pattern requires square holes with vertical walls.

The opaque aperture was constructed from tungsten of thickness 1 mm, corresponding to an attenuation of 97%. A photograph of this aperture is shown in FIG. 18. The pattern was obtained by laser drilling a tungsten sheet. For a highly transparent aperture (FIG. 19), tungsten foil of thickness 100 μm was used, corresponding to an attenuation of 29%. The pattern was obtained by laser ablating a thin frame on the border of each hole. Mechanical strength was provided by an aluminium backing plate.

To facilitate mounting and alignment of the coded apertures, a specialized aluminium gamma camera frame was designed (FIG. 20). The frame matched the mounting mechanism of the gamma camera, and allowed for the attachment of separate carriages. Each carriage was rotatable through 90° and supported a coded aperture and lead shielding tubes. The carriages allowed the coded apertures to be centered with respect to the axis of rotation, and to be set parallel to the crystal of the gamma camera.

The above-described experimental set-up yielded the following results:

A. Simulation

The rotational technique for reducing near-field artifacts was applied to all coded aperture images and, in the below-described figures, the maximum pixel value and acquisition time refers to the encoded image, prior to rotation.

For the Simulation count statistics were implemented by altering the number of counts that were acquired by a given pixel of the encoded image, in accordance with the Poisson distribution. This results in a projected aperture pattern that is less recognizable, and can be expected to degrade the highly transparent coded aperture images of our previous work [12].

A line set at 45° to the horizontal was used as a digital phantom, in order to allow for comparison with the experimental data. All simulation factors were held constant, apart from the acquisition bit-depth (FIGS. 21a, b and c). Count statistics require an increased bit-depth in order for the SNR to not be adversely affected. Nevertheless, the simulation results show that the concept of high-transparency coded apertures remains applicable.

B. Experimentation

For all measurements, a $^{99m}$Tc 1 ml syringe source was positioned at a distance of 20 cm from the Philips Axis crystal. The sensitivity of the system—comprising the gamma camera and the highly transparent coded aperture—was examined in terms of count rate measured in counts per second (cps), as a function of source activity. The results are presented in Table 1 below and provide an indication of the region of optimal count rate, which was of greater interest than optimal sensitivity.

TABLE 1

| Gamma camera sensitivity for a 29% attenuation aperture | | |
|---|---|---|
| Source Activity | | Count Rate |
| (MBq) | (μCi) | ($10^3$ cps) |
| 3.1 | 85 | 41.3 |
| 3.7 | 100 | 48.8 |
| 12.5 | 339 | 111.4 |
| 22.1 | 598 | 129.0 |
| 24.4 | 660 | 123.0 |
| 37.8 | 1021 | 108.1 |
| 78.1 | 2110 | 41.6 |

Based on the count rate data, a 24.4 MBq (660 μCi) source was prepared. The low energy high resolution (LEHR) collimator image provides a point of reference (FIG. 22).

The opaque coded aperture results in some noise at a maximum pixel count of 286. This is evident in FIG. 23 while, at a maximum pixel count of 3270 the noise is reduced (FIG. 24), but near-field artifacts remain evident. Coded aperture resolution is superior to that of the LEHR collimator, as is particularly evident where the syringe tapers on the upper right hand side of the image. Note that both the collimator and the coded aperture images were acquired at identical geometries, however LEHR resolution would be expected to improve as the source approaches the crystal.

The highly transparent coded aperture results in significant noise at a maximum pixel count of 285 (FIG. 25). The noise clearly decreases at a maximum pixel count of 8248 (FIG. 26) and is comparable to the improvement predicted by the simulations.

C. Discussion of Experimental Results

The experimental results support the concept of high-transparency coded apertures. It is possible not only to obtain an image with a highly transparent coded aperture, but also to acquire an image of a quality that approaches that of an opaque coded aperture based purely on the bit-depth or in other words count statistics of the acquisition.

The practicality of highly transparent coded apertures must be viewed in terms of source activity and image acquisition time. The optimal count rate for the Philips Axis gamma camera and the 29% attenuation coded aperture occurs in the 22.2 MBq (600 µCi) range, for a source at a distance of 20 cm from the crystal. If not limited by the gamma camera, a source in the 222 MBq (6 mCi) range would, for example, allow for practical 16-bit image acquisition times, but this may not be clinically realizable.

With the use of a higher sensitivity gamma camera, highly transparent coded apertures could be used without a decrease in the SNR. Coded aperture manufacture would be greatly simplified, and thickness artifacts reduced. Alternatively, opaque coded apertures allow for the rapid acquisition of low source activity images, but thickness artifacts remain.

In conclusion, planar phantom study results, for a 24.4 MBq (660 µCi) syringe source positioned at a distance of 20 cm from the Philips Axis crystal, show that a coded aperture with an attenuation of 29% allows an image to be acquired, and that the image approaches that of an opaque coded aperture as the bit-depth of the acquisition increases. The result is not only comparable to that predicted by the simulations, but also serves to support the novel concept of highly transparent coded apertures in diagnostic nuclear medicine.

Furthermore, a coded aperture which has a projection of the smallest hole occupying the same area as a single pixel of the detector can also be applied to a coded aperture which has an attenuation percentage that is low relative to the state of the art, such as 50% or less. In fact, the combination of the two inventions may give the optimum result for the application of coded apertures in nuclear medicine imaging.

References

[1] Accorsi, R., Gasparini, F., and Lanza, R. A coded aperture for high-resolution nuclear medicine planar imaging with a conventional Anger camera: experimental results. *IEEE Transactions on Nuclear Science*, 48(6):2411-2417, December 2001.

[2] In't Zand, J. Coded aperture imaging in high-energy astronomy. Laboratory for High Energy Astrophysics (LHEA), http://lheawww.gsfc.nasa.gov/docs/cai/coded_i-ntr.html, 1996. Last date of access: Mar. 30, 2004.

[3] Accorsi, R., Gasparini, F., and Lanza, R. Optimal coded aperture patterns for improved SNR in nuclear medicine imaging. *Nuclear Instruments and Methods in Physics Research*, A474:273-284, 2001.

[4] Accorsi, R., and Lanza, R. Near-field artifact reduction in planar coded aperture imaging. *Journal of Applied Optics*, 40(26):4697-4705, 2001.

[5] Starfield, D. M., Rubin, D. M., and Marwala, T. Near-field artifact reduction using realistic limited-field-of-view coded apertures in planar nuclear medicine imaging. *IFMBE Proceedings of the World Congress on Medical Physics and Biomedical Engineering*, 1558-1561, Seoul, August 2006.

[6] Accorsi, R. Design of near-field coded aperture cameras for high-resolution medical and industrial gamma-ray imaging. *PhD Thesis*, Massachusetts Institute of Technology, June 2001.

[7] Shepp, L. A., and Logan, B. F. The Fourier reconstruction of a head section. *IEEE Transactions on Nuclear Science*, NS-21(3):21-43, June 1974.

[8] Accorsi, R., Autiero, M., Celentano, L., Laccetti, P., Lanza, R. C., Marotta, M., Mettivier, G., Montesi, M. C., Riccio, P., Roberti, G., Russo, P. Toward a Medipix2 coded aperture gamma microscope. *IEEE Nuclear Science Symposium Conference Record*, 4:2461-2464, October 2004.

[9] Accorsi, R. A 15-µm resolution imager for soft X-ray emitters. *IEEE Nuclear Science Symposium Conference Record*, 5:2975-2979, October 2004.

[10] Cherry, S. R., Sorenson, J. A., Phelps, M. E. Physics in Nuclear Medicine—$3^{rd}$ ed. *Saunders*, Philadelphia, 2003.

[11] Choi, Y., Koo, J.-Y., and Lee, N.-Y. Image reconstruction using the wavelet transform for positron emission tomography. *IEEE Transactions on Medical Imaging*, 20(11):1188-1193, 2001.

[12] Starfield, D. M., Rubin, D. M., and Marwala, T. High transparency coded apertures in planar nuclear medicine imaging. In *Proceedings of the 29th Annual International Conference of the IEEE EMBS*, 4468-4471, Lyon, August 2007.

The invention claimed is:

1. A coded aperture mask for use in radiation-based medical imaging comprising a sheet of radiation opaque mask material having a series of apertures extending therethrough, the thickness of mask material having an attenuation percentage of less than 50%.

2. A coded aperture mask for use in radiation-based medical imaging as claimed in claim 1 in which the mask material has an attenuation percentage of less than 30%.

3. A coded aperture mask for use in radiation-based medical imaging as claimed in any one of claims 2 and 1 in which the coded aperture mask is used for imaging gamma-rays.

4. A coded aperture mask for use in radiation-based medical imaging as claimed in claim 3 in which the sheet of radiation opaque mask material is a sheet of metal selected from the group consisting of tungsten, gold, lead and platinum.

5. A coded aperture mask for use in radiation-based medical imaging as claimed in claim 4 in which, when the metal is tungsten, it has a thickness of 100 µm (which is largely transparent) for imaging Technetium-99 m (which has an energy of 140 keV).

6. A coded aperture mask for use in radiation-based medical imaging as claimed in claim 4 in which, when the metal is gold, it has a thickness of 90 µm (which is largely transparent) for imaging Technetium-99 m (which has an energy of 140 keV).

7. A coded aperture mask for use in radiation-based medical imaging as claimed in claim 4 in which, when the metal is lead, it has a thickness of 130 µm (which is largely transparent) for imaging Technetium-99 m (which has an energy of 140 keV).

8. A coded aperture mask for use in radiation-based medical imaging as claimed in claim 4 in which, when the metal is platinum, it has a thickness of 80 µm (which is largely transparent) for imaging Technetium-99 m (which has an energy of 140 keV).

9. A coded aperture mask for use in radiation-based medical imaging as claimed in claim 1 in which the coded aperture has a projection of the smallest hole occupying the same area as a single pixel of a detector.

10. A coded aperture mask for use in radiation-based medical imaging as claimed in claim 1 in which multiple coded apertures are arranged in an array which is from a 3 by 3 to a 5 by 5 array.

11. A coded aperture mask for use in radiation-based medical imaging as claimed in claim 10 in which a radiation attenuating tube extends about each coded aperture mask in the direction of the axes of the apertures therein.

12. A coded aperture mask for use in radiation-based medical imaging as claimed in claim 11 in which each tube extends from either side of the respective masks.

13. A coded aperture mask for use in radiation-based medical imaging as claimed in claim 12 in which each tube has parallel sides.

14. A coded aperture mask for use in radiation-based medical imaging as claimed in claim 11 in which the masks are carried on one sheet of material.

15. A coded aperture mask for use in radiation-based medical imaging as claimed in claim 11 in which the coded aperture masks are made of tungsten and the radiation attenuating tubes are made of lead.

16. A coded aperture mask for use in radiation-based medical imaging as claimed in claim 15 in which the tungsten has a thickness of 100 μm.

17. A coded aperture mask for use in radiation-based medical imaging as claimed in claim 15 in which the lead has a thickness of 1 to 2 mm.

18. A coded aperture mask for use in radiation-based medical imaging as claimed in claim 17 in which each tube extends up to 50 cm on either side of the array.

19. A coded aperture mask for use in radiation-based medical imaging as claimed in claim 17 in which each tube extends up to at least 10 cm on either side of the array.

20. A coded aperture mask for use in radiation-based medical imaging as claimed in claim 1 in which the masks are configured for gamma rays.

21. A coded aperture mask for use in radiation-based medical imaging as claimed in claim 20 in which the gamma rays have an energy of 140 keV.

22. A radiation-based medical imaging system comprising a radiation source, a coded aperture mask as claimed in claim 1 and a radiation detector.

23. A radiation-based medical imaging system as claimed in claim 22 in which the radiation source is a gamma-ray radiation source.

24. A radiation-based medical imaging system as claimed in claim 22 in which the radiation detector is a gamma camera.

25. A radiation-based medical imaging system as claimed in claim 24 in which, the gamma camera is a 16 bit gamma camera.

26. A coded aperture mask for use in radiation-based medical imaging comprising a sheet of radiation opaque mask material having a series of apertures extending therethrough, the thickness of mask material having an attenuation percentage of less than 75% and the coded aperture having a projection of the smallest hole occupying the same area as a single pixel of a detector.

* * * * *